(12) United States Patent
Hamamah et al.

(10) Patent No.: US 8,956,865 B2
(45) Date of Patent: Feb. 17, 2015

(54) METHODS OF GROWING AN EMBRYO TO A BLASTOCYST STAGE OF DEVELOPMENT

(75) Inventors: Samir Hamamah, Montpellier (FR); Said Assou, Montpellier (FR)

(73) Assignees: Institut National de la Sante et de la Recherche Medicale (INSERM), Paris (FR); Universite Montpellier 1, Montpellier Cedex (FR); Centre Hospitalier Universitaire de Montpellier, Montpellier Cedex (FR)

( * ) Notice: Subject to any disclaimer, the term of this patent is extended or adjusted under 35 U.S.C. 154(b) by 0 days.

(21) Appl. No.: 13/816,311

(22) PCT Filed: Aug. 11, 2011

(86) PCT No.: PCT/EP2011/063821
§ 371 (c)(1),
(2), (4) Date: Feb. 11, 2013

(87) PCT Pub. No.: WO2012/020077
PCT Pub. Date: Feb. 16, 2012

(65) Prior Publication Data
US 2013/0143317 A1   Jun. 6, 2013

(30) Foreign Application Priority Data
Aug. 11, 2010   (EP) .................................. 10305882

(51) Int. Cl.
*C12N 5/02* (2006.01)
*C12N 5/073* (2010.01)
*A61D 19/00* (2006.01)
*C12N 5/0735* (2010.01)

(52) U.S. Cl.
CPC ............. *C12N 5/0604* (2013.01); *A61D 19/00* (2013.01); *C12N 5/0605* (2013.01); *C12N 5/0606* (2013.01); *C12N 2502/02* (2013.01)
USPC .......................................... 435/366; 435/373

(58) Field of Classification Search
CPC .. A61D 19/00; C12N 5/0604; C12N 2502/02; C12N 5/0606; C12N 5/0605
See application file for complete search history.

(56) References Cited

FOREIGN PATENT DOCUMENTS

EP   0 340 934 A1   11/1989

OTHER PUBLICATIONS

Ponchio et al., Cytotherapy (2000) vol. 2, No. 4, 281-286.*
Quinn et al., "Beneficial effects on coculture with cumulus cells on blastocyst formation in a prospective trial with supernumerary human embryos", Journal of Assisted Reproduction and Genetics, 1996, pp. 9-14, vol. 13, No. 1.
Farouk et al., "In Vitro Development of Mouse Pronuclear Embryos to Blastocysts in Sequential Media With and Without Co-Culture of Autologous Cumulus Cells", Journal of Reproduction and Development, Oct. 2008, pp. 385-390, vol. 54, No. 5.
Sandor et al., "Deep-freezing of bovine embryos derived from in vitro fertilization (IVF)", Magyar Allatorvosok Lapja, 1996, pp. 69-71, vol. 51, No. 2.
Gilchrist et al., "Oocyte maturation: Emerging concepts and technologies to improve developmental potential in vitro", Theriogenology, Dec. 6, 2006, pp. 6-15, vol. 67, No. 1, Los Altos, CA.
Vanhoutte et al., "Prematuration of human denuded oocytes in a three-dimensional co-culture system: Effects on meiosis progression and develpmental competence", Human Reproduction, Mar. 2009, pp. 658-669, vol. 24, No. 3.
Assou et al., "Human cumulus cells as biomarkers for embryo and pregnancy outcomes", Molecular Human Reproduction, Apr. 29, 2010, pp. 531-538, vol. 16, No. 8, Oxford University Press, GB.

* cited by examiner

Primary Examiner — Doug Schultz
(74) Attorney, Agent, or Firm — Whitham Curtis Christofferson & Cook, PC

(57) ABSTRACT

The present invention relates generally to the fields of reproductive medicine. More specifically, the present invention relates to a novel human embryo co-culture system to improve human embryo growth in vitro and, consequently, increase pregnancy rates in infertile women undergoing in vitro fertilization (IVF) treatment. More particularly, the present invention relates to a method of growing an embryo to a blastocyst stage of development comprising the step of coculturing said embryo in the presence of a population of cumulus cells.

8 Claims, No Drawings

METHODS OF GROWING AN EMBRYO TO A BLASTOCYST STAGE OF DEVELOPMENT

FIELD OF THE INVENTION

The present invention relates generally to the fields of reproductive medicine. More specifically, the present invention relates to a novel human embryo co-culture system to improve human embryo growth in vitro and, consequently, increase pregnancy rates in infertile women undergoing in vitro fertilization (IVF) treatment.

BACKGROUND OF THE INVENTION

In vitro fertilization is a powerful and widely used technique for the treatment of infertility. In this procedure, human eggs are retrieved and mixed with sperm in a culture dish to allow fertilization. The embryos are then transferred to the uterus on day 2/3, when it has between 4 and 8 cells respectively or day 5 or 6 at blastocyst stage. This technique is used for women with, for example, damaged or absent Fallopian tubes, endometriosis, male factor infertility and unexplained infertility. However, the implantation rate varies between 5% and 30%.

Under in vivo conditions, the embryo reaches the uterus at a blastocyst stage of development. Accordingly, embryo coculture techniques, used successfully in animals, represent an effort to improve the culture media for embryos such that a greater proportion of embryos will reach the blastocyst stage for improving the implantation and pregnancy rates. In addition, if coculture results in a higher implantation rate, fewer embryos could be transferred at each cycle, resulting in a decreased incidence of multiple pregnancies. A variety of coculture techniques have been therefore investigated, involving the use of feeder cell layers derived from a range of tissues, including the use of human reproductive tissues (i.e., endometrium). However, no standardized method of coculture has emerged and the optimal system for preimplantation human embryo culture has not yet been determined.

SUMMARY OF THE INVENTION

The present invention relates to a method of growing an embryo to a blastocyst stage of development comprising the step of coculturing said embryo in the presence of a population of cumulus cells.

DETAILED DESCRIPTION OF THE INVENTION

The concept and technology of the present invention involves growing embryos on human cumulus cells (hCCs). The idea is that these cells, which are sometimes referred to as "helper" cells, will stimulate early embryos development by adding growth factors, or some other beneficial effect. Another potential application of coculture with hCCs for human IVF program, is that of culturing embryos to the blastocyst stage and then performing blastocyst transfer on day 5 or day 6. This allows best embryo selection that has been able to survive through the early cleavage stages of the first week of development. It is generally very difficult to get good numbers of high quality blastocysts when culturing in simples culture media. hCCs are somatic cells found closely associated with the developing oocyte in the ovarian follicle. hCCs are stimulated to grow, differentiate and luteinize by endocrine, paracrine and autocrine factors. The major functions of hCCs include the production of steroids, as well as a myriad of growth factors to interact with the oocyte during its development within the ovarian follicle. However, after ovulation, the hCCs produce progesterone that may maintain a potential pregnancy. Accordingly, the present invention relates to a method for in vitro coculture of human embryo on human cumulus cells (hCCs).

Methods of Growing an Embryo to a Blastocyst Stage of Development

The present invention relates to a method of growing an embryo to a blastocyst stage of development comprising the step of coculturing said embryo in the presence of a population of cumulus cells.

As used herein the term "embryo» refers to a zygote or post-zygotic derivatives of a fertilized egg. The term "embryo" therefore refers to any entity in the pie-embryonic stage following fertilization of the egg. The term thus includes a fertilized egg and a zygote. According to the invention, the embryo is from any mammalian species (humans, sheep, cows, pigs, horses . . . ), but preferably is a human embryo.

Embryos may be generated in vitro by any of the techniques well known in the art, such as in vitro fertilization (IVF), including IVF performed by simple mixing of oocyte and sperm or by intracytoplasmic injection of sperm into an oocyte, and nuclear transfer.

For in vitro fertilization (IVF), oocytes retrieved from a female are fertilized using sperm retrieved from a male (for example, by simple mixing of oocyte and sperm or by intracytoplasmic injection of sperm into the oocyte), and embryonic development is initiated in vitro. Protocols and methods for IVF are well established in the art for a variety of mammals, including humans (see, for example, Boiso et al. Reprod Biomed Online. 2002; 5:328-350; Frydman et al. Hum Reprod. 1988; 3:559-561; Tarin and Pellicer. Ann Acad Med Singapor 1992; 21:492-497; Kenny. Br J Obstet Gynaecol. 1995; 102:317-325; Mansour. Hum Reprod Update. 1998; 4:43-56; and Evans et al. Obstet Gynecol Surv. 1980; 35:7181), mice (see, for example, Yanagimachi. Hum Reprod. 1998; 13:87-98 and Sato et al. Horm Res. 1995; 44 Suppl 2:4-8), sheep (see, for example, Armstrong et al. Reprod Fertil Dev. 1997; 9:333-339), cows (see, for example, Hoshi. Theriogenology. 2003; 59:675-685 and Marquant-Leguienne and Humblot. Theriogenology. 1998; 49:3-11), hamsters (see, for example, Bavister. Gamete Res. 1989; 23: 139-158); horses (see, for example, Squires. Vet Clin North Am Equine Pract. 1996; 12:31-45 and Hinrichs. Theriogenology 1998; 49:13-21) and pigs (see, for example, Niemann and Rath. Theriogenology. 2001; 56:1291-1304 and Robl and First. J ReprodFertil Suppl. 1985; 33:101-114).

IVF protocols may be generally summarized as having four stages, as follows. Stage One: Ovarian Stimulation and Monitoring. In order to maximize the patient's chances for successful fertilization, a patient undergoing IVF takes hormones in the form of injections to increase the number of eggs produced in a given month. Monitoring is performed to continuously follow a woman's ovarian response, allowing the physician to adjust and time medication dosage appropriately. Stage Two: Ovum Retrieval. With the patient sedated and comfortable, the ova or eggs are retrieved through the vagina under ultrasound guidance. Stage Three: Culture and Fertilization. The oocytes are fertilized with sperm from the male partner. At times, the sperm are put down on top of the oocyte. In other cases, especially when there are less than one million living sperm, ICSI or intracytoplasmic sperm injection is used catch a single sperm and inject it directly into the oocyte. Stage Four: Embryo Transfer. Either three or four of the best embryos are transferred directly into the uterus and allowed to implant. The remaining healthy embryos may be 25 cryopreserved (frozen) The pregnancy test is performed 11 days after embryo transfer. In a good program with a high quality laboratory, a woman under the age of 40 should become pregnant approximately 50% of the time.

For nuclear transfer, the nucleus of a donor cell (e.g., a 30 somatic cell) is transferred into an enucleated oocyte, for example, by cell-fusion between an enucleated oocyte and a nucleus donor cell. Following nuclear transfer the oocyte is activated to stimulate embryonic development. In other nuclear transfer methods, the nucleus of a donor cell (e.g., a 35 somatic cell) is transferred into an enucleated fertilized oocyte, without the need for subsequent activation of the oocyte. Various types of cells can be employed as donors for nuclei to be transferred into oocytes, including adult, fetal or embryonic cells, at various stages of differentiation, ranging 40 from undifferentiated to fully differentiated, in various cell cycle stages, e.g. both quiescent and proliferating cells, and obtained form either somatic or germline tissues. Donor nuclei may be introduced into oocytes by means of fusion, induced electrically or chemically, or by microinjection.

Protocols and methods for nuclear transfer are well established in the art (see, for example Wilmut et al. Nature 1997; 385:810-813; Prather and First. J. Reprod. Fert. 1990; Suppl 41:125-134; Cibelli et al. Science 1998; 280:1256-8; U.S. Pat. No. 6,600,087; Dominko et al. Biol. Reprod 1999; 50 6:1496-1502; Published PCT application WO 99/37143; Published PCT application WO 98/07841; Published PCT application WO 97/07669; Published PCT application WO 98/30683; Published PCT application WO 98/39416; U.S. Pat. Nos. 6,147,276; 6,781,030; 55 6,635,802; and 5,945, 577). For example, nuclear transfer protocols are well established in the art for sheep (see, for example, Campbell et al. Nature 1996; 380: 64-66 and Liu et al. Mol Reprod Dev 1997; 47:255-264), cows (see, for example, Cibelli et al. Science 1998; 280:1256-8; 60 Bordignon et al. Mo I Reprod Dev 1998; 49:29-36; Tanaka et al. Jpn. J. Vet. Res. 1995; 43:135-143; Kato et al. Science 1998; 282:2095-2098; Wells et al. Biol. Reprod. 1999; 60:996-1005; Kubota et al. Proc. Natl. Acad. Sci. USA 2000; 97:990-995; and Vignon et al. Life Sciences 1998; 321:735- 65 745), rabbits (see, for example, Collas et al. Biol Reprod 1992; 46:492-500) goats (see, for example, Baguisi et al. Nature Biotech 1999; 17:456-461 and Keefer et al. 5/o/ogyq/" Reproduction 2001; 64:849-856), pigs (see, for example, U.S. Pat. No. 6,700,037 and Liu et al. Int. J. Dev. Biol. 1995; 39:639-644), and mice (see, for example, Wakayama et al. Nature 1998; 394:369-374 and Wakayama and Yanagimachi. Nature Genetics 1999; 22:127-128).

Alternatively, embryos generated in vivo may be retrieved from a pregnant mammal (e.g., a female laboratory mouse sacrificed 1.5 days post coitus).

As used herein, the term "blastocyst" refers to the structure formed in the early embryogenesis of mammals, after the formation of the morula. It possesses an inner cell mass (ICM), or embryoblast, which subsequently forms the embryo, and an outer layer of cells, or trophoblast, which later forms the placenta. The trophoblast surrounds the inner cell mass and a fluid-filled blastocyst cavity known as the blastocoele. The human blastocyst comprises 70-100 cells. Blastocyst formation begins at day 5 after fertilization in humans when the blastocoele opens up in the morula.

The term "cumulus cell" as used herein refers to any cultured or non-cultured cell isolated from cells and/or tissue surrounding an oocyte. Persons skilled in the art can readily identify cumulus cells. Examples of methods for isolating and/or culturing cumulus cells are discussed in Damiani et al., 1996, Mol. Reprod. Dev. 45: 521-534; Long et al., 1994, J Reprod. Pert. 102: 361-369; and Wakayama et al., 1998, Nature 394: 369-373, each of which is incorporated herein by reference in its entireties. Cumulus cells may be isolated from ovarian follicles at any stage of development, including primordial follicles, primary follicles, secondary follicles, growing follicles, vesicular follicles, maturing follicles, mature follicles, and graafian follicles. Cumulus cells may be isolated from oocytes in a number of manners well known to a person of ordinary skill in the art. For example, cumulus cells can be separated from oocytes by pipeting the cumulus cell/oocyte complex through a small bore pipette, by exposure to hyaluronidase, or by mechanically disrupting (e.g. vortexing) the cumulus cell/oocyte complex. Additionally, exposure to $Ca^{++}/Mg^{++}$ free media can remove cumulus from immature oocytes. Also, cumulus cell cultures can be established by placing imatured oocytes in cell culture media. Once cumulus cells are removed from media containing increased LH/FSH concentrations, they can to attach to the culture plate.

According to an embodiment of the invention, the cumulus cells may be isolated from any species, but in a particular embodiment, the cumulus cells according to the invention are human cumulus cells. In another particular embodiment, the cumulus cells are derived form a cumulus cell line.

An embodiment of the invention relates to a method of growing an embryo to a blastocyst stage of development, said method comprising a step of culturing said embryo on a cell culture surface coated with a layer of cumulus cells.

The term "cell culture surface" or "cell culture matrix" refers to every type of surface or matrix suitable for cell culture. The term "cell culture surface" includes but is not limited to tissue culture plate, dish, well or bottle. In a particular embodiment, the culture surface is plastic surface of the culture plate, dish, well or bottle. The cell culture surface is to be compatible with the coating of cumulus cells. According to an embodiment of the invention, the cell culture surface is selected in the manner that cumulus cells may naturally adhere on it. Various materials of cell culture surface may be selected. Examples of such materials include but are not limited to tissue culture dishes or dishes coated with collagen.

Typically, as described in EXAMPLE, to obtain a layer of cumulus cells on a cell culture surface, the cumulus cells are first coated on the cell culture surface with a culture medium containing collagen. After a sufficient time for allowing adhesion of cumulus cell on the cell culture surface, the culture medium containing collagen is removed and replace by a medium that allows expansion of said cumulus cell.

In a particular embodiment, cumulus cells are previously treated to stop their proliferation before to in be in contact with the embryo. Therefore, the cumulus cells are inactivated by gamma irradiation or with a cell cycle blocking agent.

In accordance with the present invention, the culture conditions are also important for growing the embryo to a blastocyst stage of development. During culturing, variables such as temperature and $CO_2$ levels can be controlled to maximize the growing of the embryo. For example, the optimum temperature for the development of an embryo is from about 32° C. and about 40° C., preferably from about 35° C. and 39° C., with a temperature of 37° C. being even more preferred. The optimum $CO_2$ levels in the culturing environment for the development of an embryo is from about 1% $CO_2$ to about 10% $CO_2$, more preferably from about 3% $CO_2$ to about 8% $CO_2$, and even more preferably about 5% $CO_2$.

Suitable media for growing embryos are well known in the art. For example, culture media are now available that allow embryos to progress to blastocysts at rates comparable with those occurring within the uterus (Summers M, Biggers J D 2003 Chemically defined media and the culture of mammalian preimplantation embryos: historical perspective and current issues. Human Reprod Update 9:557-582) raising the hope that such embryos will be free of the epigenetic marks introduced as a result of the stress of in vitro culture. Many of these media are based rather loosely on the concentrations of ions, amino acids, and sugars found in the reproductive tract of the female at the time of egg release, fertilization, and development (Gardner D, Lane M 1998 Culture of viable human blastocysts in defined sequential serum free media. Hum Reprod 13:148-160). Typically, culture media containing a phosphate buffer or Hepes organic buffer are used for procedures that involve handling of gametes outside of the incubator, flushing of follicles and micromanipulation. Most culture media utilize a bicarbonate/CO2 buffer system to keep PH in the range of 7.2-7.4. The osmolarity of the culture medium must be in the range of 275-290 mosmol/kg. Embryos could also be cultured under paraffin oil, which prevents evaporation of the medium preserving a constant osmolarity. The oil also minimizes fluctuations of pH and temperature when embryos are taken out of the incubator for microscopic assessment. Paraffin oil can be toxic to gametes and embryos; therefore, batches of oil must be screened and tested on mouse embryos before use in culture of human embryos.

The medium is composed of 99% water. Purity of the water is crucial, and is achieved by ultrafiltration.

Culture medium also contains a protein source, such as albumin or synthetic serum that are added in concentrations of 5 to 20% (w/v or v/v, respectively). As source of salt is also added to the medium such as Nacl, Kcl, Kh2PO4, Cacl22H2o, Mgso47H2O, or NaHCO3. Culture medium also contains a carbohydrates source, since carbohydrates are present in the female reproductive tract. Together with the amino acids they are the main energy source for the embryo. Culture media that support the development of zygotes up to 8-cells contain pyruvate and lactate. Some commercial media are glucose free, while others add a very low concentration of glucose to supply the needs of the sperm during conventional insemination. Media that support the development of 8-cell embryos up to the blastocyst stage contain pyruvate and lactate in low concentrations and a higher concentration of glucose. Supplement of the culture medium with amino acids is also necessary for embryo development. Media that support the development of zygotes up to 8-cells are supplemented with non essential amino acids such as proline, serine, alanine, aspargine, aspartate, glycine, and glutamate. Media that support the development of 8-cell embryos up to the blastocyst stage are supplemented with essential amino acids such ascystine, histadine, isolucine, leucine, lysine, methionine, valine, argentine, glutamine, phenylalanine, therionine, tryptophane. The culture medium may also contain vitamins.

The culture medium may also contain antibiotics. The majority of ART laboratories use indeed culture media containing antibiotics to minimize the risks of microbial growth. The most commonly used antibiotics being Penicillin (β-lactam Gram-positive bacteria disturbs cell wall integrity) and Streptomycin (Aminoglycoside Gram-negative bacteria disturbs protein synthesis).

Three examples of sequential media for embryo development are: G1/G2 (Gardner et al, 1998 Hum. Reprod. 13, 3434); Universal IVF Medium/MS (Bertheussen et al., 1997); and PI/Blastocyst Medium (Behr et al., 1998 Am. Soc. Rep. Med. 0-262). Interestingly, medium M3 is a modification of Ham's F-10 and F-12, while Blastocyst Medium is a modification of Ham's F-10). Media for culturing embryo are commercially available from Origio (Denmark), Vitrolife (Sweden), Sage Biopharma (USA), Irvine Scientific (USA).

Also provided in accordance with certain embodiments of the present invention, is a method of increasing the in vivo implantation potential of an in vitro fertilization embryo. "Implantation potential" is the ability of the embryos to implant in the uterus. This method includes carrying out one of the above-described embodiments for growing an embryo to a blastocyst stage of development, such that complete hatching of the embryo in culture is achieved or hatching is enhanced, compared to other IVF methods. In accordance with certain embodiments of this method, the balstocyst is then introduced into the uterus of a mammalian host, such than enhanced implantation of the embryo is achieved. In some embodiments, complete hatching of the embryo in vitro correlates with establishment of a viable pregnancy.

In some embodiments of the present invention, a method of increasing the live birth potential of an in vitro fertilized mammalian embryo is provided. "Live birth potential" refers to the ability of an embryo to yield a live birth. The method comprises growing an embryo to a blastocyst stage of development, as described above, such that enhanced hatching potential or complete hatching of the embryos in culture is achieved. The blastocyst is then transferred to the uterus of a mammalian host; and the embryo is allowed to implant and grow in vivo, such that the ability of the embryo to yield a live birth is enhanced relative to that of an embryo that is not cultured according to the invention.

The method of the invention is also particularly suitable for limiting multiple pregnancies because it can provides a higher implantation rate, as above described and therefore fewer embryos could be transferred at each cycle, resulting in a decreased incidence of multiple pregnancies.

Methods of Maintaining the Undifferentiated State in Culture of a Population of Pluripotent Stem Cell A further aspect of the invention relates to a method of maintaining the undifferentiated state in culture of a population of pluripotent stem cells comprising the step of coculturing said population of pluripotent stems cells in presence of a population of cumulus cells.

As used herein, the term "human pluripotent stem cell" refers to any human precursor cell that has the ability to form any adult cell. In a particular embodiment, human pluripotent stem cells include but are not limited to embryonic stem cells (hES cells) or human induced pluripotent stem cells (human iPS cells).

As used herein, the term "human embryonic stem cells" or "hES cells" or "hESC" refers to human precursor cells that have the ability to form any adult cell. hES cells are derived from fertilized embryos that are less than one week old. According to an embodiment of the invention, hES cells may be selected from any hES cell lines. Examples of hES cell lines include but are not limited to, SA-01, VUB-01, H1 (Thomson J A et al 1998), and H9 (Amit M et al. 2000). According to the invention hES cells are not previously cultured in the presence of LIF as described in the international patent application WO2002/097068. Moreover, according to the invention it shall be understood that hES cells are not previously differentiated in embryoid bodies as described in Metallo C M. et al. (2007) or in Ji L; et al. (2006).

As used herein, the term "human induced pluripotent stem cells" or "human iPS cells" or "human iPSCs" refers to a type of human pluripotent stem cell artificially derived from a human non-pluripotent cell (e.g. an adult somatic cell).

Human induced pluripotent stem cells are identical to human embryonic stem cells in the ability to form any adult cell, but are not derived from an embryo. Typically, a human induced pluripotent stem cell may be obtained through the induced expression of Oct3/4, Sox2, Klf4, and c-Myc genes in any adult somatic cell (e.g. fibroblast). For example, human induced pluripotent stem cells may be obtained according to the protocol as described by Takahashi K. et al. (2007), by Yu et al. (2007) or else by any other protocol in which one or the other agents used for reprogramming cells in these original protocols are replaced by any gene or protein acting on or transferred to the somatic cells at the origin of the iPS lines. Basically, adult somatic cells are transfected with viral vectors, such as retroviruses, which comprises Oct3/4, Sox2, Klf4, and c-Myc genes. According to an embodiment of the invention human iPS cells may be selected from any human iPS cell lines. Examples of human iPS cell lines include but are not limited to clones 201B (Takahashi et al., 2007) and iPS (Foreskin or IMR90)-1-MCB-1 (Yu et al., 2007).

Cumulus cells are the same as described for the method of growing embryo to a blastocyst stage of development (see supra).

An embodiment of the invention relates to a method of maintaining the undifferentiated state in culture of a population of pluripotent stem cells, said method comprising a step of culturing said population of pluripotent stem cells on a cell culture surface coated with a layer of cumulus cells.

Said layer of cumulus cells may be obtained as described for the method of growing embryo to a blastocyst stage of development (see supra).

In accordance with the present invention, the culture conditions are also important in maintaining the undifferentiated state in culture of a population of pluripotent stem cell. During culturing, variables such as cell density, temperature and $CO_2$ levels can be controlled to maximize the development of populations of pluripotent stem cells. For example, the density of cells in an pluripotent stem cell culture can affect the spontaneous differentiation of said population. As such, the optimum cell density for the growth of a pluripotent stem cell population is from about 1 pluripotent stem cell to about 10,000 pluripotent stem cells per cm2, more preferably from about 1 pluripotent stem cell to about 2000 pluripotent stem cells per cm2, and even more preferably from about 100 to about 1000 pluripotent stem cells per cm2. In one embodiment, the pluripotent stem cells are cultured as a single cell suspension. The optimum temperature for the development of an pluripotent stem cell population is from about 32° C. and about 40° C., preferably from about 35° C. and 39° C., with a temperature of 37° C. being even more preferred. The optimum $CO_2$ levels in the culturing environment for the development of pluripotent stem cell populations is from about 1% $CO_2$ to about 10% $CO_2$, more preferably from about 3% $CO_2$ to about 8% $CO_2$, and even more preferably about 5% $CO_2$.

Suitable media for culturing pluripotent stem cells include Dulbeco's Modified Eagle Media (Invitrogen, Carlsbad, Calif.). The skilled artisan will appreciate that a wide range of media suitable for culturing pluripotent stem cells in vitro are available, e.g., Specialty Media (Millipore Corporation, Billerica, Mass.); Resgro™ (Millipore Corporation, Billerica, Mass.); StemXvivo (R&D Systems, Minneapolis, Minn.). The media may be supplemented with serum, e.g. fetal bovine serum, ES qualified serum (Invitrogen, Carlsbad, Calif), antibiotics, e.g. Pen Strep (Invitrogen, Carlsbad, Calif.), non-essential amino acids (Invitrogen, Carlsbad, Calif.) and glutamine, e.g. Glutamax-1® (Invitrogen, Carlsbad, Calif.).

Some ESC cultures may be further supplemented with leukemia inhibitory factor, e.g., Esgro® (Millipore Corporation, Billerida, Mass.).

The invention will be further illustrated by the following examples. However, these examples should not be interpreted in any way as limiting the scope of the present invention.

EXAMPLE 1

Isolation of Human Cumulus Cells

Cumulus cells were obtained from consecutive patients with their informed consent according to the Guidelines of Assisted Reproduction Center, Hôpital Arnaud de Villeneuve; Montpellier. After examination of the cumulus mass appearance, the human cumulus cells (hCCs) are mechanically separated from the oocyte by using two needles. One needle placed on the hCCs layer to keep the oocyte in place and the other needle, is used to quickly cut off as much as possible of the cell layer, without touching the oocyte. Aspirate the cell with as little medium as possible and transfer these cells into the prepared medium.

EXAMPLE 2

Culture and Amplification of hCCs

In our initial experiment, hCCs were cultured in Dulbecco's modified Eagle's medium (DMEM) with 10% fetal calf serum (FCS) and 10 ng/ml fibroblast growth factor (bFGF) and with gelatin (0.1%) coated plates. Using this cultivation protocol, hCCs adhered to surface at 4 hrs after inoculation. Medium was replaced three times a week until confluence reaches 80%. Cells were passaged every 5-7 days enzymatically with 0.25% trypsin/EDTA. The CC line were adapted to growth on a this condition (>12 passages).

Serum (FCS) is an undefined substance with multiple factors that might influence cell function and the reliance on animal products limits the clinical application. For this reason, we optimized cultivation protocols for long-term cultivation of hCCs on animal free condition. We coated culture plates with HP01 medium containing human collagen I-III at 10 μg/cm$^2$ during two hours. We removed carefully the adhesion solution and replaced it by defined SPE-IV expansion medium (clinical grade human albumin, synthetic iron carrier, rh-insulin, nucleosides, L-glutamine, -monothioglycerol, synthetic lipids, alpha-MEM). This culture medium contains growth factors (rhIGF-I: 25 ng/ml and rh-b-FGF: 0,33 ng/ml). The cell concentration is fixed at 1.000 cells/cm$^2$. We changed completely the medium four times a week until confluence reaches 70-80%.

In conclusion, we have now developed and analyzed a newly hCCs line that contains chromosomal stability. These hCCs line were adapted to growth on a human collagen substrate in animal free defined medium (>10 passages). This growth system reduces exposure of hCCs to animal ingredients, thereby limiting the risk of pathogenic contamination.

EXAMPLE 3

Preparation of CC Feeder Layer

Monolayer of hCCs (passage 5) were cultured to confluency and treated with 10 μg/ml mitomycin-C for 2 h or by irradiation. Following treatments, cells were detached with Tryple and seeded onto culture dishes.

EXAMPLE 4

Human Embryonic Stem Cells (HESCS) Grew on the hCCs Feeder Layer

The propagation and pluripotent characteristics of a human embryonic stem cell (hESC) line were studied in prolonged culture in on hCCs. We reported that hESC cultured on hCCs were indistinguishable by multiple criteria (morphology, pluripotency markers) from hESC cultured on a fibroblast feeder layer. We showed that hESC grown on hCCs maintain markers of pluripotency, including expression of cell surface proteins (SSEA3, SSEA4, TRA-1-60, TRA-1-81). The morphology and molecular characteristics of the cells are similar as compared to the hESC cultured on fibroblast feeder cells.

In conclusion, the hCCs support undifferentiated hESC growth. hESC lines readily adapt to these feeders and maintain the typical morphology of undifferentiated hESC cultures. The hESC also continued to express pluripotent markers, including TRA-1-60, SSEA3, SSEA-4, Tra-1-81 and CD24.

EXAMPLE 4

Global Gene Expression Analysis Validates hCCs for "Embryo" Propagation

Genome-wide gene expression profiles of HFF feeder cells and hCCs express 62% of gene expression similarity. The correlation coefficients among the two samples were high, with only a small number of genes showing statistically significant differential expression.

REFERENCES

Throughout this application, various references describe the state of the art to which this invention pertains. The disclosures of these references are hereby incorporated by reference into the present disclosure.

The invention claimed is:

1. A method of growing an embryo to a blastocyst stage of development comprising the step of
    coculturing said embryo in vitro in the presence of a population of cumulus cells, wherein said cumulus cells are derived from a cumulus cell line obtained by
        isolating cumulus cells from cells and/or tissue surrounding an oocyte, and culturing isolated cumulus cells in vitro on a collagen-coated cell culture surface in defined medium,
    wherein said embryo and said cumulus cells are human.

2. The method according to claim 1 wherein said embryo is cultured on a cell culture surface coated with a layer of cumulus cells.

3. The method according to claim 1 wherein the cumulus cells are previously treated to stop their proliferation before contacting the embryo.

4. The method according to claim 1 wherein said embryo is generated in vitro by a technique selected from the group consisting of in vitro fertilization (IVF), intracytoplasmic injection of sperm into an oocyte, and nuclear transfer.

5. The method of claim 4, wherein said IVF is performed by mixing of oocyte and sperm.

6. The method of claim 1, wherein said defined medium is free of animal serum.

7. The method of claim 1, wherein said step of culturing includes a step of passaging said cumulus cells for at least 10 passages.

8. The method of claim 1, wherein said cell line is chromosomally stable.

* * * * *